(12) United States Patent
Tal et al.

(10) Patent No.: US 11,241,250 B2
(45) Date of Patent: Feb. 8, 2022

(54) VASCULAR TREATMENT DEVICES AND METHODS

(71) Applicant: Merit Medical Systems, Inc., South Jordan, UT (US)

(72) Inventors: Michael G. Tal, Woodbridge, CT (US); John P. Marano, Jr., Madison, CT (US)

(73) Assignee: Merit Medical Systems, Inc., South Jordan, UT (US)

( * ) Notice: Subject to any disclaimer, the term of this patent is extended or adjusted under 35 U.S.C. 154(b) by 162 days.

(21) Appl. No.: 14/218,527

(22) Filed: Mar. 18, 2014

(65) Prior Publication Data

US 2014/0207052 A1 Jul. 24, 2014

Related U.S. Application Data

(62) Division of application No. 13/295,518, filed on Nov. 14, 2011, now Pat. No. 8,696,645.

(60) Provisional application No. 61/413,895, filed on Nov. 15, 2010.

(51) Int. Cl.
| | | |
|---|---|---|
| *A61B 17/12* | (2006.01) | |
| *A61B 17/3207* | (2006.01) | |
| *A61B 17/00* | (2006.01) | |

(52) U.S. Cl.
CPC .... *A61B 17/3207* (2013.01); *A61B 17/12013* (2013.01); *A61B 17/320758* (2013.01); *A61B 17/12186* (2013.01); *A61B 2017/00778* (2013.01); *A61B 2017/1205* (2013.01); *A61B 2017/320733* (2013.01)

(58) Field of Classification Search
CPC .... A61B 17/320758; A61B 17/320725; A61B 17/3207; A61B 2017/320733; A61B 17/320708; A61B 17/320783; A61B 17/12013; A61B 2017/320716; A61B 2017/320741; A61B 2017/320791; A61B 17/32; A61B 2017/320004; A61B 2017/320008; A61B 2017/320012
See application file for complete search history.

(56) References Cited

U.S. PATENT DOCUMENTS

| 2,212,477 A | 8/1940 | Mayer |
| 3,405,712 A | 10/1968 | Pierick |
| 3,530,492 A | 9/1970 | Ferber |

(Continued)

FOREIGN PATENT DOCUMENTS

| CA | 2405273 | 4/2001 |
| CN | 2148536 | 12/1993 |

(Continued)

OTHER PUBLICATIONS

International Search Report and Written Opinion dated May 23, 2012 for PCT Application No. PCT/US2011/060859.

(Continued)

*Primary Examiner* — James D Ponton
(74) *Attorney, Agent, or Firm* — Stoel Rives LLP (57) ABSTRACT

An apparatus for performing a vascular treatment includes an intraluminal member that is controllingly moved during the vascular treatment. The intraluminal member of the vascular treatment device can be connected to a motor. The intraluminal member may be configured to retain endothelium during the vascular treatment procedure.

20 Claims, 6 Drawing Sheets

(56) References Cited

U.S. PATENT DOCUMENTS

| | | | |
|---|---|---|---|
| 3,631,847 A | 1/1972 | Hobbs, II | |
| 3,633,566 A | 1/1972 | Grabhorn | |
| 4,278,085 A | 7/1981 | Shim | |
| 4,403,611 A | 9/1983 | Babbit | |
| 4,577,514 A | 3/1986 | Bradley | |
| 4,586,921 A | 5/1986 | Berson | |
| 4,728,319 A | 3/1988 | Masch | |
| 4,790,812 A * | 12/1988 | Hawkins, Jr. | A61B 17/221 604/22 |
| 4,854,325 A | 8/1989 | Stevens | |
| 4,857,046 A * | 8/1989 | Stevens | A61B 1/12 604/22 |
| 4,867,156 A | 9/1989 | Stack et al. | |
| 4,876,109 A | 10/1989 | Mayer et al. | |
| 4,906,236 A | 3/1990 | Alberts et al. | |
| 4,936,845 A | 6/1990 | Stevens | |
| 5,022,399 A | 6/1991 | Biegeleisen | |
| 5,026,384 A | 6/1991 | Farr et al. | |
| 5,047,013 A | 9/1991 | Rossdeutscher | |
| 5,074,871 A | 12/1991 | Groshong | |
| 5,078,723 A | 1/1992 | Dance et al. | |
| 5,087,244 A | 2/1992 | Wolinsky et al. | |
| 5,087,265 A | 2/1992 | Summers | |
| 5,100,425 A | 3/1992 | Fischell et al. | |
| 5,116,350 A * | 5/1992 | Stevens | A61B 17/320758 606/159 |
| 5,135,517 A | 8/1992 | McCoy | |
| 5,176,646 A | 1/1993 | Kuroda | |
| 5,269,794 A | 12/1993 | Rexroth | |
| 5,304,115 A * | 4/1994 | Pflueger | A61B 17/22012 604/22 |
| 5,330,481 A | 7/1994 | Hood | |
| 5,356,418 A | 10/1994 | Shturman | |
| 5,370,653 A | 12/1994 | Cragg | |
| 5,415,636 A | 5/1995 | Forman | |
| 5,423,799 A * | 6/1995 | Shiu | A61B 17/320758 606/159 |
| 5,449,351 A | 9/1995 | Zohmann | |
| 5,549,601 A | 8/1996 | McIntyre et al. | |
| 5,578,014 A | 11/1996 | Erez et al. | |
| 5,611,357 A | 3/1997 | Suval | |
| 5,628,730 A | 5/1997 | Shapland et al. | |
| 5,632,755 A | 5/1997 | Nordgren et al. | |
| 5,675,228 A | 10/1997 | O'Bryan | |
| 5,707,355 A | 1/1998 | Zimmon | |
| 5,709,657 A | 1/1998 | Zimmon | |
| 5,716,366 A | 2/1998 | Yates | |
| 5,766,191 A | 6/1998 | Trerotola | |
| 5,776,153 A | 7/1998 | Rees | |
| 5,836,905 A | 11/1998 | Lemelson et al. | |
| 5,843,103 A * | 12/1998 | Wulfman | A61B 17/320758 606/159 |
| 5,851,208 A * | 12/1998 | Trott | A61B 17/32002 606/80 |
| 5,882,329 A * | 3/1999 | Patterson | A61B 17/3207 604/500 |
| 5,893,858 A | 4/1999 | Spitz | |
| 5,902,266 A | 5/1999 | Leone et al. | |
| 5,908,395 A | 6/1999 | Stalker | |
| 5,911,700 A | 6/1999 | Mozsary et al. | |
| 5,921,963 A | 7/1999 | Erez et al. | |
| 5,976,164 A | 11/1999 | Bencini et al. | |
| 6,015,420 A * | 1/2000 | Wulfman | A61B 17/320758 604/22 |
| 6,048,332 A | 4/2000 | Duffy et al. | |
| 6,066,153 A * | 5/2000 | Lev | A61B 17/32002 606/180 |
| 6,090,118 A | 7/2000 | McGuckin, Jr. | |
| 6,129,734 A | 10/2000 | Shturman et al. | |
| 6,159,196 A | 12/2000 | Ruiz | |
| 6,165,187 A | 12/2000 | Reger | |
| 6,171,234 B1 | 1/2001 | White et al. | |
| 6,193,735 B1 | 2/2001 | Stevens | |
| 6,193,736 B1 | 2/2001 | Webler | |
| 6,231,518 B1 | 5/2001 | Grabek et al. | |
| 6,258,087 B1 | 7/2001 | Edwards et al. | |
| 6,261,272 B1 | 7/2001 | Gross | |
| 6,273,882 B1 | 8/2001 | Whittier et al. | |
| 6,290,675 B1 | 9/2001 | Vujanic et al. | |
| D450,843 S | 11/2001 | McGuckin, Jr. et al. | |
| 6,346,095 B1 | 2/2002 | Gross | |
| 6,369,039 B1 | 4/2002 | Palasis et al. | |
| 6,402,745 B1 | 6/2002 | Wilk | |
| 6,443,929 B1 | 9/2002 | Kuracina | |
| 6,482,215 B1 | 11/2002 | Shiber | |
| 6,484,727 B1 | 11/2002 | Vaska et al. | |
| 6,517,528 B1 | 2/2003 | Pantages et al. | |
| 6,520,928 B1 | 2/2003 | Junior | |
| 6,544,221 B1 | 4/2003 | Kokish et al. | |
| 6,547,776 B1 | 4/2003 | Gaiser et al. | |
| 6,572,630 B1 * | 6/2003 | McGuckin, Jr. | A61B 17/320758 606/159 |
| 6,575,932 B1 | 6/2003 | O'Brien et al. | |
| 6,602,264 B1 | 8/2003 | McGuckin, Jr. | |
| 6,645,221 B1 | 11/2003 | Richter | |
| 6,673,025 B1 | 1/2004 | Richardson et al. | |
| 6,679,886 B2 | 1/2004 | Weikel et al. | |
| 6,733,473 B1 | 5/2004 | Reifart et al. | |
| 6,824,550 B1 | 11/2004 | Noriega et al. | |
| 6,824,551 B2 | 11/2004 | Trerotola | |
| 6,852,118 B2 | 2/2005 | Shturman et al. | |
| 7,025,774 B2 | 4/2006 | Freeman et al. | |
| 7,083,643 B2 | 8/2006 | Whalen et al. | |
| 7,108,704 B2 | 9/2006 | Trerotola | |
| 7,211,073 B2 | 5/2007 | Fitzgerald et al. | |
| 7,285,126 B2 | 10/2007 | Sepetka et al. | |
| 7,402,155 B2 | 7/2008 | Palasis | |
| 7,402,320 B2 | 7/2008 | Mirizzi et al. | |
| 7,419,482 B2 | 9/2008 | Nash | |
| 7,644,715 B2 | 1/2010 | Hayes et al. | |
| 7,670,328 B2 | 3/2010 | Miller | |
| 7,713,231 B2 | 5/2010 | Wulfman | |
| 7,819,887 B2 | 10/2010 | McGuckin, Jr. et al. | |
| 7,862,575 B2 | 1/2011 | Tal | |
| 7,967,834 B2 | 6/2011 | Tal et al. | |
| 3,029,560 A1 | 10/2011 | Bates et al. | |
| 8,029,491 B2 | 10/2011 | Aboul-Hosn | |
| 8,038,664 B2 | 10/2011 | Miller | |
| 8,052,645 B2 | 11/2011 | Slate et al. | |
| 8,123,669 B2 | 2/2012 | Siess et al. | |
| 8,696,645 B2 | 4/2014 | Tal et al. | |
| 9,585,667 B2 | 3/2017 | Tal et al. | |
| 2001/0004700 A1 | 6/2001 | Honeycutt et al. | |
| 2002/0010418 A1 | 1/2002 | Lary et al. | |
| 2002/0072704 A1 | 6/2002 | Mansouri-Riuz | |
| 2002/0077589 A1 | 6/2002 | Tessari | |
| 2002/0077594 A1 | 6/2002 | Chien et al. | |
| 2002/0173812 A1 | 11/2002 | McGuckin et al. | |
| 2002/0188276 A1 | 12/2002 | Evans et al. | |
| 2003/0004568 A1 | 1/2003 | Ken et al. | |
| 2003/0045860 A1 | 3/2003 | Leu | |
| 2003/0078606 A1 * | 4/2003 | Lafontaine | A61B 17/3207 606/159 |
| 2003/0120256 A1 | 6/2003 | Lary et al. | |
| 2003/0225435 A1 | 12/2003 | Huter et al. | |
| 2004/0092967 A1 | 5/2004 | Sancoff et al. | |
| 2004/0147934 A1 | 7/2004 | Kiester | |
| 2004/0153110 A1 | 8/2004 | Kurz et al. | |
| 2004/0220519 A1 | 11/2004 | Wulfman et al. | |
| 2004/0254566 A1 | 12/2004 | Plicchi | |
| 2005/0055040 A1 | 3/2005 | Tal | |
| 2005/0055041 A1 | 3/2005 | Woods | |
| 2005/0085836 A1 | 4/2005 | Raymond | |
| 2005/0096642 A1 | 5/2005 | Appling | |
| 2005/0165354 A1 | 7/2005 | Schwartz | |
| 2006/0013548 A1 | 1/2006 | Mishra et al. | |
| 2006/0015169 A1 | 1/2006 | Letort | |
| 2006/0095015 A1 | 5/2006 | Hobbs | |
| 2006/0106407 A1 | 5/2006 | McGuckin, Jr. et al. | |
| 2006/0217692 A1 | 9/2006 | Neuberger | |
| 2006/0224110 A1 | 10/2006 | Scott | |
| 2006/0259052 A1 | 11/2006 | Pintor et al. | |

(56) References Cited

U.S. PATENT DOCUMENTS

| | | |
|---|---|---|
| 2007/0112308 A1 | 5/2007 | Kay |
| 2007/0239140 A1 | 10/2007 | Chechelski et al. |
| 2007/0282359 A1 | 12/2007 | Tal |
| 2008/0009791 A1 | 1/2008 | Cohen et al. |
| 2008/0033458 A1 | 2/2008 | McLean |
| 2008/0108971 A1 | 5/2008 | Klein |
| 2008/0140101 A1 | 6/2008 | Carley |
| 2008/0172012 A1 | 7/2008 | Hiniduma-Lokuge |
| 2008/0243068 A1 | 10/2008 | Ramzipoor et al. |
| 2008/0275432 A1 | 11/2008 | Castro et al. |
| 2008/0300571 A1 | 12/2008 | LePivert |
| 2008/0300574 A1 | 12/2008 | Belson et al. |
| 2009/0018486 A1 | 1/2009 | Goren et al. |
| 2009/0137906 A1 | 5/2009 | Maruyama |
| 2009/0222003 A1 | 9/2009 | Otley |
| 2009/0270888 A1 | 10/2009 | Patel et al. |
| 2009/0270889 A1 | 10/2009 | Tal et al. |
| 2010/0069760 A1 | 3/2010 | Tang |
| 2010/0125276 A1 | 5/2010 | Palermo |
| 2010/0217306 A1 | 8/2010 | Raabe et al. |
| 2010/0217313 A1 | 8/2010 | Raabe et al. |
| 2010/0268076 A1 | 10/2010 | Gat et al. |
| 2010/0274178 A1 | 10/2010 | LePivert |
| 2011/0046543 A1 | 2/2011 | Brandeis |
| 2011/0060277 A1 | 3/2011 | Lilley |
| 2011/0066142 A1 | 3/2011 | Tal |
| 2012/0130410 A1 | 5/2012 | Tal et al. |
| 2012/0130411 A1 | 5/2012 | Tal |
| 2012/0130415 A1 | 5/2012 | Tal et al. |
| 2012/0197200 A1 | 8/2012 | Belson |
| 2012/0265168 A1 | 10/2012 | Horowitz |
| 2014/0207052 A1 | 7/2014 | Tal et al. |

FOREIGN PATENT DOCUMENTS

| | | |
|---|---|---|
| CN | 1330913 A | 1/2002 |
| DE | 10059742 | 6/2002 |
| EP | 0501081 | 9/1992 |
| FR | 2651682 | 3/1991 |
| JP | 2003/299662 | 10/2003 |
| JP | 2003-523803 A | 12/2003 |
| JP | 2004508096 | 3/2004 |
| JP | 2004508096 A | 3/2004 |
| JP | 2008520351 A | 6/2008 |
| JP | 2009/078150 | 4/2009 |
| JP | 2009254874 A | 11/2009 |
| JP | 2010-503479 A | 2/2010 |
| JP | 2011-512983 A | 4/2011 |
| WO | WO 97/14362 | 4/1997 |
| WO | 98012967 A1 | 4/1998 |
| WO | 9947056 A1 | 9/1999 |
| WO | 0007500 A1 | 2/2000 |
| WO | 0108561 A1 | 2/2001 |
| WO | WO 01/54754 A1 | 8/2001 |
| WO | 2004112569 A2 | 12/2004 |
| WO | 2006055265 A1 | 5/2006 |
| WO | 2006111503 A2 | 10/2006 |
| WO | 2008005888 A2 | 1/2008 |
| WO | WO 2008/033983 | 3/2008 |
| WO | WO 2009/109967 | 9/2009 |
| WO | 2010056714 A1 | 5/2010 |
| WO | 2010093630 A2 | 8/2010 |
| WO | 2010096717 A1 | 8/2010 |
| WO | 2010112618 A1 | 10/2010 |
| WO | WO 2012/068162 | 5/2012 |
| WO | WO 2012/068165 | 5/2012 |
| WO | WO 2012/068166 | 5/2012 |

OTHER PUBLICATIONS

International Search Report and Written Opinion dated May 30, 2012 for PCT Application No. PCT/US2011/060860.
International Search Report and Written Opinion dated May 30, 2012 for PCT Application No. PCT/US2011/060855.
International Search Report dated Jan. 11, 2008 for PCT Application No. PCT/US2007/078367.
Written Opinion dated Jan. 11, 2008 for PCT Application No. PCT/US2007/078367.
Williams et al. "Sclerosant Treatment of Varicose Veins and Deep Vein Thrombosis," Archives of Surgery, vol. 119, No. 11, Nov. 1984.
International Search Report dated Nov. 2, 2005 for PCT Application No. PCT/US04/15858.
Written Opinion dated Nov. 2, 2005 for PCT Application No. PCT/US04/15858.
VenaSeal Closure System. Viewed online Mar. 1, 2019 at http://medtronicendovenous.com/patients/7-2-venaseal-closure-procedure/. Medtronic. Minneapolis, MN.
ScleroSafe. Viewed online Mar. 1, 2019 at http://www.vvtmed.com/products/sclerosafe/. VVT Medical. Kfar Sava, Israel.
V-Block System Viewed online Mar. 1, 2019 at http://www.vvtmed.com/products/v-block/. VVT Medical. Kfar Sava, Israel.
European Search Report dated Jul. 30, 2019 for E011841604.9.
Office Action dated Mar. 6, 2019 for U.S. Appl. No. 15/194,083.
Office Action dated Jun. 28, 2019 for U.S. Appl. No. 15/194,083.
Office Action dated Jan. 8, 2020 for U.S. Appl. No. 15/194,083.

* cited by examiner

VASCULAR TREATMENT DEVICES AND METHODS

RELATED APPLICATIONS

The present application is a divisional of U.S. patent application Ser. No. 13/295,518, filed Nov. 14, 2011, which claims priority to U.S. Provisional Application No. 61/413,895, filed on Nov. 15, 2010, entitled "VASCULAR ABLATION APPARATUS AND METHOD." The content of each of these applications is hereby incorporated by reference in its entirety.

BACKGROUND OF THE INVENTION

Field of the Invention

This specification relates to the field of vascular treatment.

Description of the Related Art

Sclerotherapy can be used to treat blood vessels, blood vessel malformations, and similar problems in other body systems, such as the lymphatic system, and has been used in various forms for over 150 years. In its more modern form, sclerotherapy has been used since the 1960's, in Europe, for treating various vein conditions such as; varicose veins, reticular veins, spider veins of the leg, and also some fine facial veins.

Sclerotherapy can be used to treat these conditions by instigating vascular fibrosis and obliteration in response to irreversible endothelial cellular destruction and exposure of the underlying subendothelial cell layer. This destruction is usually caused by the injection of a sclerosant into the vein. However, if the injected sclerosant is too weak, there may be no endothelial injury at all. If the sclerosant is a little stronger, the varicose vessel is damaged, but recanalization occurs and an incompetent pathway for retrograde blood flow persists. Finally, if the injected sclerosant is too strong, the varicose vessel endothelium is destroyed, but adjacent vessels that are not targeted for treatment may also be damaged by the sclerosant.

The requirement for an ideal strength of the sclerosant is complicated by the constant flow of blood through the vein that is being treated. This flow simultaneously dilutes, and thereby weakens, the sclerosant, while also transporting the sclerosant to other parts of the vascular system.

Thus, improved methods and devices for treating the vascular system are desired.

SUMMARY OF THE INVENTION

In one embodiment, a vascular treatment apparatus comprises an elongated intraluminal member shaped and dimensioned for passage through blood vessels of a subject. The intraluminal member may include a proximal end and a distal end, wherein the distal end comprises a vein wall disruptor. The vein wall disruptor may be configured to scrape tissue off of the inner wall of a blood vessel, and retain that tissue on the disruptor during use.

In another embodiment, a vascular treatment apparatus comprises an elongated intraluminal member shaped and dimensioned for passage through blood vessels of a subject, the intraluminal member including a proximal end and a distal end, wherein the distal end comprises a vein wall disruptor. The vein wall disruptor is configured to scrape tissue off of the inner wall of a blood vessel, and comprises structures therein forming tissue storing regions. The structures may be cavities or through holes.

In some embodiments, these apparatus may comprise a source of sclerosant and a fluid channel between the source of sclerosant and the distal end of the elongated intraluminal member.

In another embodiment, a vascular treatment method comprises advancing an elongated intraluminal member from an access site and into the vein, damaging the inner vessel wall by performing a defined movement of the portion of the intraluminal member against the vein's endothelium. The damaging comprises removing endothelium tissue from the inner vessel wall and retaining endothelium tissue on the portion of the intraluminal member while performing the defined movement.

In another embodiment, a method for permanently occluding a vein through the combined disruption of a vein vessel wall and application of a sclerosant comprises advancing an elongated intraluminal member from an access site and into the vein, wherein the intraluminal member has a portion thereof configured to produce damage to the inner vessel wall of the vein under user control when performing a defined movement, damaging the inner vessel wall by performing the defined movement of the portion of the intraluminal member against the vein's endothelium, injecting sclerosant into the vein and onto the damaged inner vessel wall, observing sclerosant exiting from the access site, and stopping injection of sclerosant in response to the observing.

In another embodiment, a method for permanently occluding a vein through the combined disruption of a vein vessel wall and application of a sclerosant comprises orienting a subject with at least one extremity below their head, advancing an elongated intraluminal member from an access site and into a vein in the at least one extremity, wherein the intraluminal member has a portion thereof configured to produce damage to the inner vessel wall of the vein under user control when performing a defined movement, re-orienting the subject with the at least one extremity approximately level with or slightly above their head, damaging the inner vessel wall by performing the defined movement of the portion of the intraluminal member against the vein's endothelium, and injecting sclerosant into the vein and onto the damaged inner vessel wall. The extremity may be an arm or a leg.

The foregoing is a summary and thus contains, by necessity, simplifications, generalization, and omissions of detail; consequently, those skilled in the art will appreciate that the summary is illustrative only and is not intended to be in any way limiting. Other aspects, features, and advantages of the devices and/or processes and/or other subject matter described herein will become apparent in the teachings set forth herein. The summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

DETAILED DESCRIPTION OF THE PREFERRED EMBODIMENT

The following description and examples illustrate preferred embodiments of the present invention in detail. Those of skill in the art will recognize that there are numerous variations and modifications of this invention that are encompassed by its scope. Accordingly, the description of a preferred embodiment should not be deemed to limit the scope of the present invention. In this description, reference is made to the drawings wherein like parts are designated with like numerals throughout.

Figure 1:
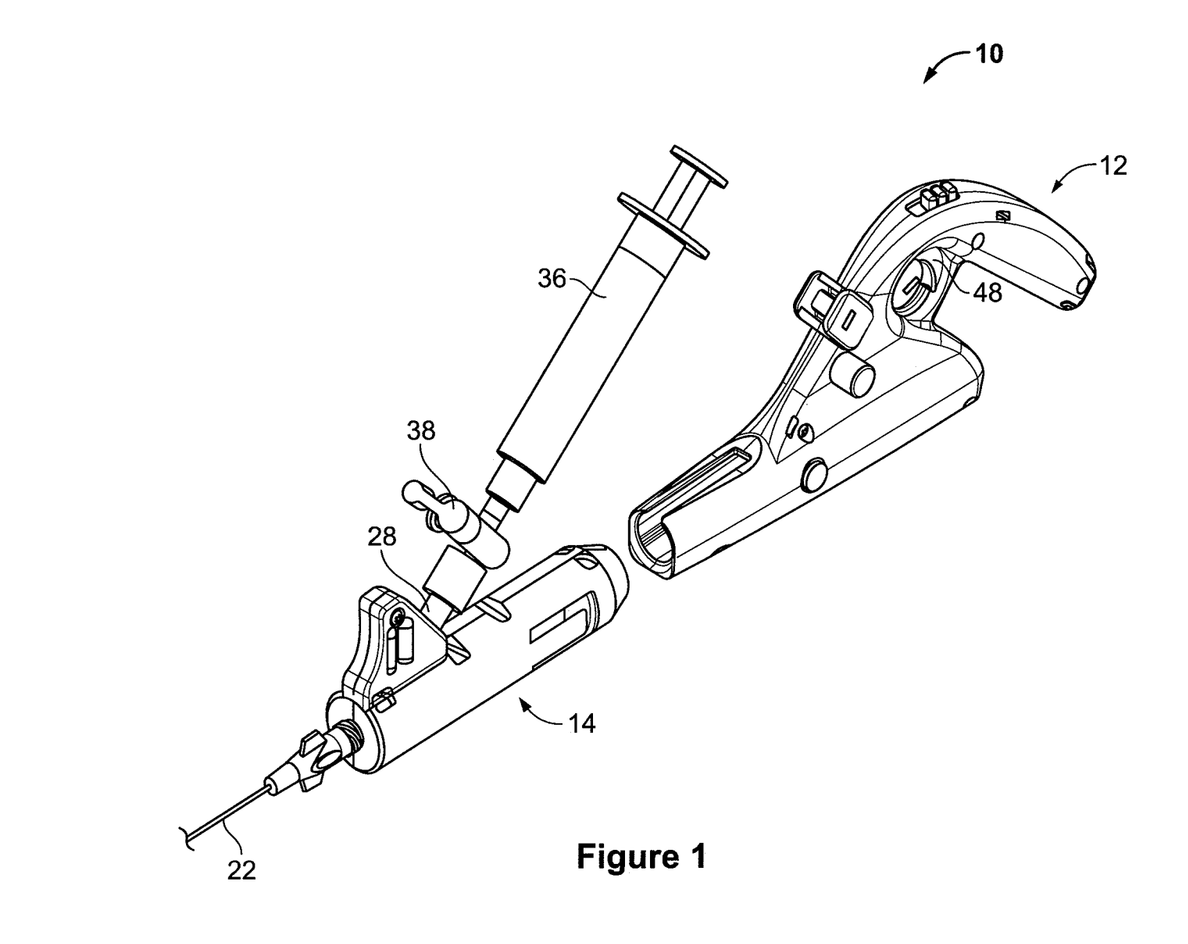
FIG. 1 shows an embodiment of an assembly of a vascular treatment device.

FIG. 1 depicts a perspective view of one embodiment of exemplary components of a vascular treatment device 10. These components can be configured to provide a range of functionalities to the vascular treatment device 10. In some embodiments, a vascular treatment device 10 can include features configured for stimulating vascular ablation, such as, for example, an intraluminal member 22, a motorized drive system, including, for example, a motor, and/or control features and/or features configured for delivering liquid sclerosant. In some embodiments described further below, the intraluminal member comprises a wire surrounded by a sheath, and the wire is rotatable within the sheath. The space between the sheath and the wire can be used as a passage to inject sclerosant as the wire rotates, and the distal end of the wire forms a vein wall disruptor.

In general, the vascular treatment device 10 of FIG. 1 is utilized by introducing the intraluminal member into a vein of a subject, where the vein is to be ablated in a treatment for varicose veins for example. The distal end of the wire is extended from the distal end of the sheath, and the wire is rotated or otherwise moved to damage the endothelium lining the inside surface of the vein. Sclerosant is also injected to the region of damage through the sheath that forms an outer portion of the intraluminal member 22. The combination of endothelium damage plus the sclerosant provides a highly effective vascular ablation procedure with a minimum amount of injected sclerosant.

As depicted in FIG. 1, a vascular treatment device can include a handle 12 and a cartridge 14. As explained below in greater detail, each of the handle 12 and cartridge 14 can include features configured for stimulating vascular ablation and/or for delivering liquid sclerosant. In one embodiment, and as depicted in FIG. 1, the handle 12 and the cartridge 14 can comprise separate pieces. In another embodiment, a handle 12 and a cartridge 14 can comprise an integrated component. A person of skill in the art will recognize that the present disclosure is not limited to a specific configuration of the handle 12 and cartridge 14 but broadly includes the range of functions and uses of a vascular therapy device.

As further depicted in FIG. 1, the cartridge 14 can be, for example, sized and shaped to engagingly connect to the handle 12. In one embodiment, and as shown in FIG. 1, this engaging connection can be achieved by fitting features of the handle 12 to features of the cartridge 14.

Figure 2A:
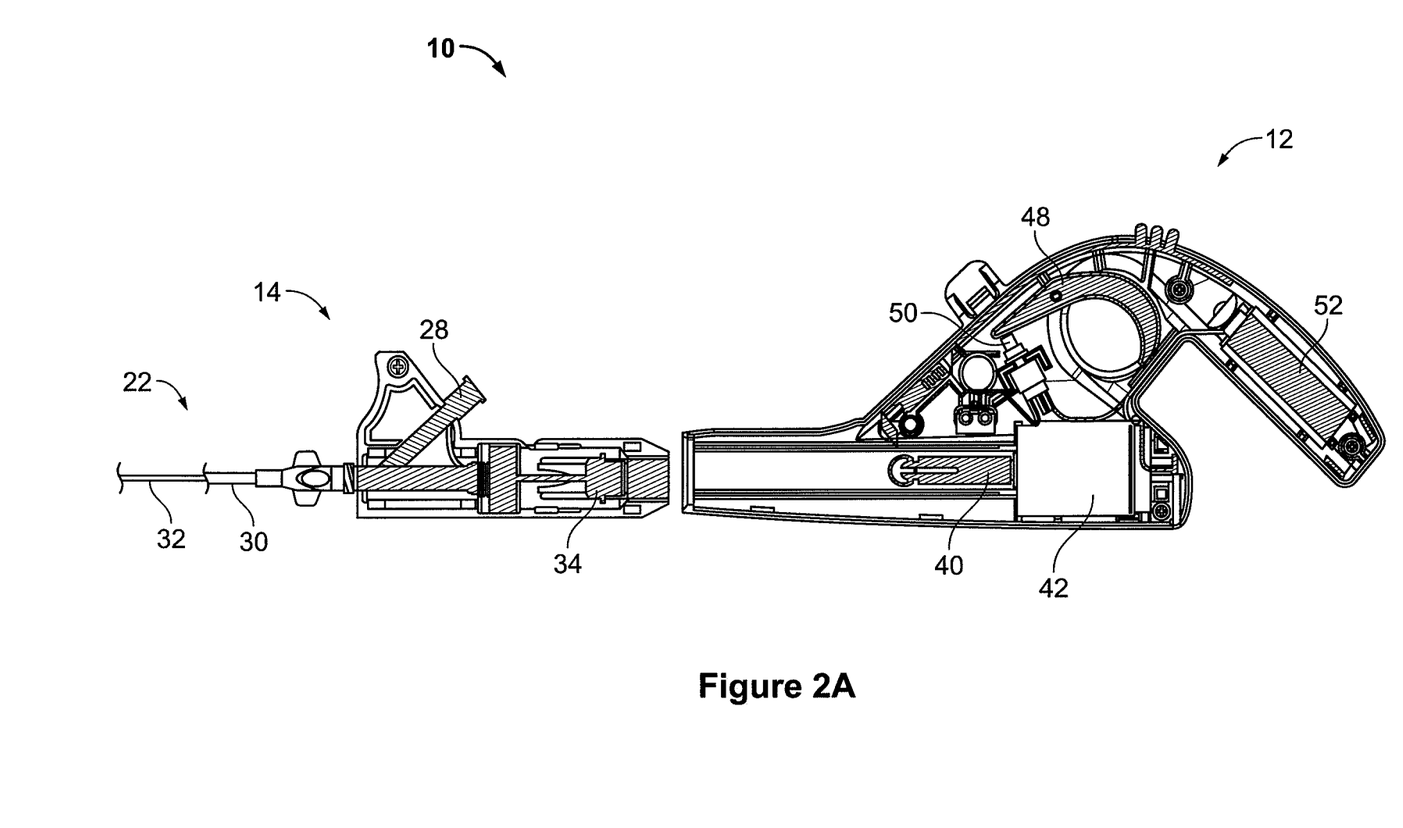
FIG. 2A illustrates a longitudinal cross-sectional view of the embodiment illustrated in FIG. 1.

FIG. 2 depicts a side cross-section view of the vascular treatment device 10 of FIG. 1. The vascular treatment device 10 depicted in FIG. 2 comprises the same features discussed in relation to FIG. 1. Referring now to both FIGS. 1 and 2, the cartridge 14 may include a sheath 30 affixed to and extending from the cartridge 14, a wire 32, and a coupling 34. The wire 32 can be, for example, fixed to the coupling 34. A person of skill in the art will recognize that the wire 32 can be affixed to the coupling 34 through a variety of techniques and methods. A person of skill in the art will further recognize that the wire 32 can be affixed to a range of features of a vascular treatment device 10 configured for driving the wire 32.

The wire 32 (and surrounding sheath) can comprise a variety of lengths. In some embodiments, a wire 32 can have a length matching the needs of the procedure. In some embodiments, a wire 32 can have a length, for example, of up to 10 cm, up to 25 cm, up to 75 cm, or up to 150 cm.

The sheath 30 can be configured to define a lumen through which the wire 32 runs, and can be configured to allow independent motion of the wire 32 within the sheath 30. The sheath 30 can have a variety of inner and outer diameters. In some embodiments, the sheath 30 can have an inner diameter ranging from approximately 0.022 inches to 0.048 inches. In some embodiments, the sheath 30 can have an outer diameter ranging from approximately 0.025 inches to 0.051 inches. In some embodiments, the outer diameter of the sheath 30 can be in the range that is, for example, consistent with the inner diameter of standard needles or vascular sheaths used for used for insertion of vascular catheters.

The sheath 30 may also include external markings at regular intervals which may guide the user to monitor the insertion or removal speed of the intraluminal member 22.

Some embodiments of a vascular treatment device 10 can be configured for use with injectant. In some embodiments, the cartridge 14 can be configured for holding an injectant such as sclerosant in a syringe 36 attached to the cartridge 14 at a coupler 28. Some embodiments of a vascular treatment device 10 and/or a cartridge 14 configured for use in connection with an injectant can be, for example, configured with valves and connectors to facilitate such use. In some embodiments, a syringe 36 can, for example, connect to a stopcock 38 on a cartridge 14. The stopcock 38 shown in FIG. 1 can be configured to allow the removal and/or attachment of a syringe to the vascular treatment device 10 during a procedure. In some embodiments, a stopcock 38 can be configured to allow reloading of fluid and/or exchanging of containers to, for example, change the injectant or the concentration of the injectant. In some embodiments, the stopcock 38 can be configured to provide additional functionality, such as, for example, mixing or aerating the injectant. The output of the coupler 28 is in fluid communication with the space between the sheath 30 and the wire 32 so that the injectant can be pushed along this space to the distal end 39-39c of the wire 32 and sheath 30 where the injectant (e.g. sclerosant) exits the sheath when installed in the vein.

Figure 2B:
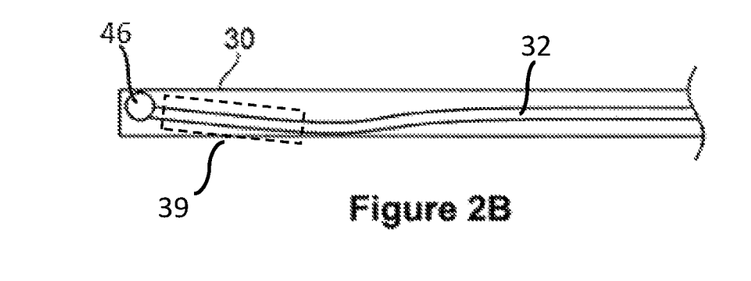
FIG. 2B illustrates the distal ends of the wire and sheath of FIG. 2A.

In use, the sheath 30 with the wire 32 inside may be introduced into the vein prior to coupling the cartridge 14 to the handle 12. At this time, the wire 32 may be fully enclosed by the sheath 30 as shown in FIG. 2B. After introduction, the cartridge 14 can be inserted into the handle 12, and the coupler 34 can engage a mating coupler 40 in the handle.

Figure 2C:
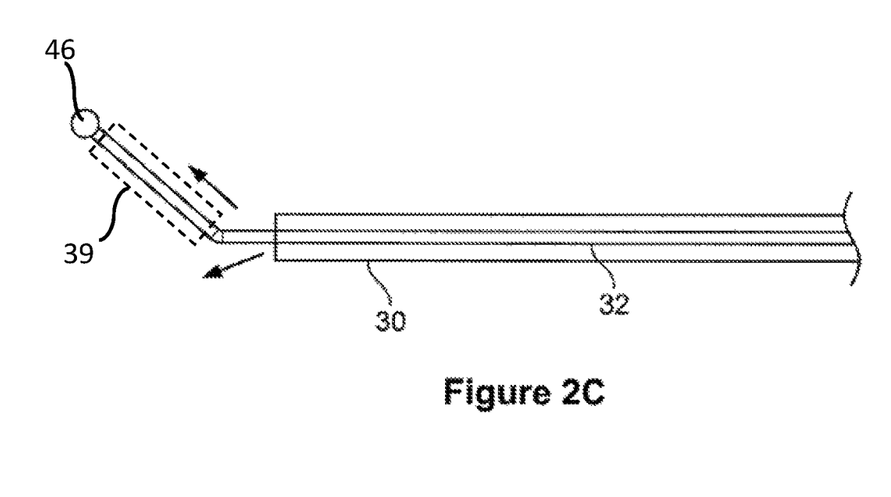
FIG. 2C illustrates the distal ends of the wire and sheath of FIG. 2A with the distal end of the wire extending out from the end of the sheath.

The coupler 34 in the cartridge which is attached to the wire 32 may be slidable within the cartridge 14, so that when the coupler 34 in the cartridge is forced into engagement with the coupler 40, the distal end 39 of the wire 32 is pushed out of the sheath 30, as shown in FIG. 2C. This exposes a portion of the wire 32 that is configured to damage the endothelium on the inner surface of the vein. The coupler 40 in the handle 12 is attached to the shaft of a motor 42 in the handle that may rotate the coupler 40, mated coupler 34, and attached wire 32 to scrape and damage the inner wall of the vein. During this process, sclerosant may be forced down the sheath, to exit the sheath in the region near the distal end 39 of the wire 32, as shown by arrows in FIG. 2C.

Motor rotation may be controlled by a trigger 48 in the handle that depresses and releases a switch 50 to start and stop motor rotation. The handle 12 may further include a power source for the motor such as battery 52.

The tips of the wire 32 can have a variety of configurations. As illustrated in FIGS. 2B and 2C, the distal end 39 of the wire 32 can have a spherical ball 46 at the tip. During rotation, this ball is the feature that does the most damage to the endothelium on the inner vessel wall. Embodiments of vascular treatment devices such as illustrated in FIGS. 1 through 2C are further described in U.S. Pat. Nos. 7,862,575 and 7,967,834 which are incorporated herein by reference in their entireties.

Although vascular ablation treatments using the above described vascular treatment device have shown dramatic improvement over prior vascular ablation methods, it has been found that the configurations of the distal ends 39 of the wire are sometimes not optimal. For example, it is advantageous if the wire 32 removes and retains endothelium as it rotates within the vein. This retention of endothelium tissue on the wire 32 appears to increase friction and result in more complete and faster damage to the inner wall of the vein. Distal ends 39a-39c that are configured to retain endothelium are described further below with respect to FIGS. 3A through 3C.

Figure 3A:
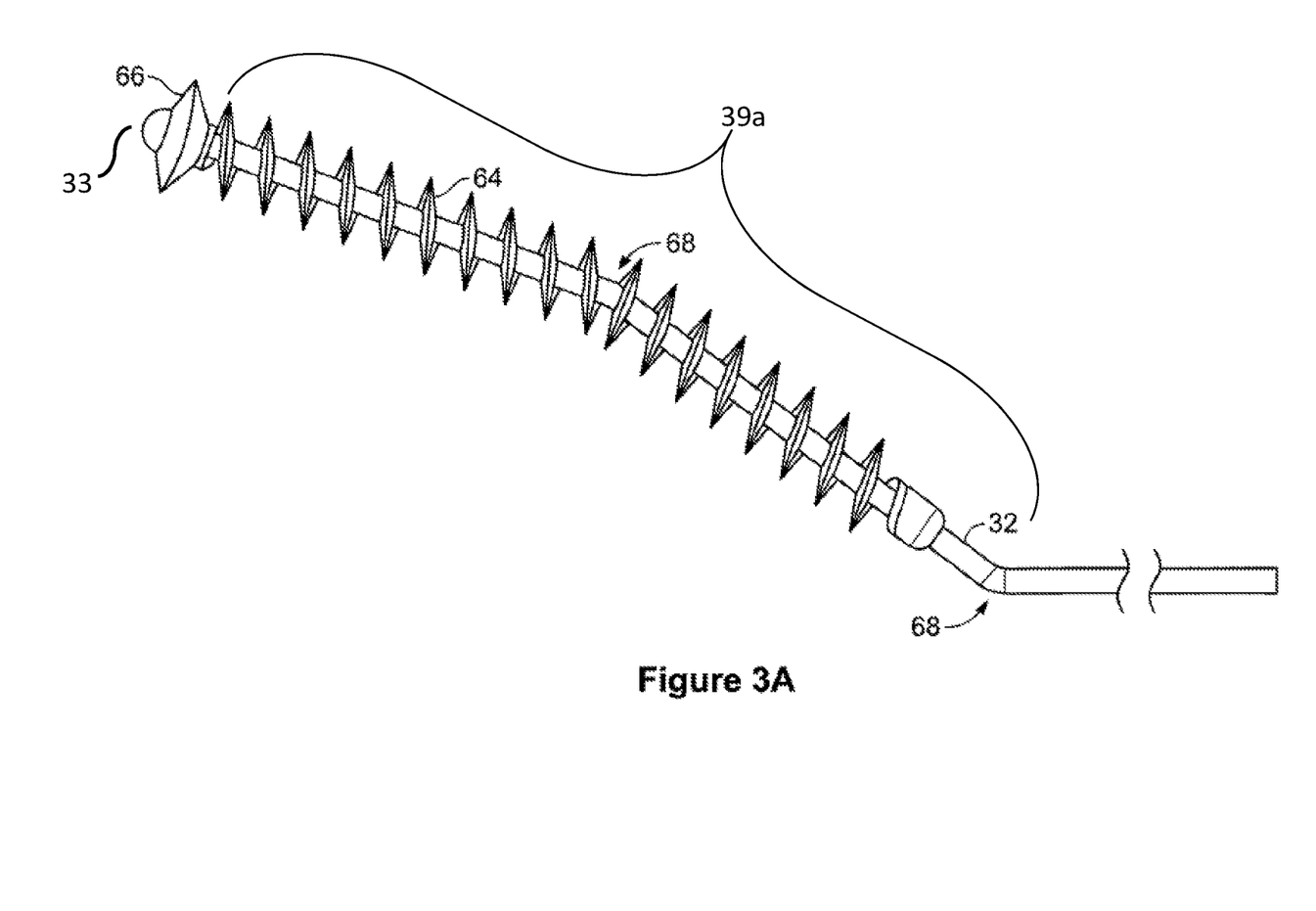
FIG. 3A illustrates an embodiment of a distal end of a wire with multiple sharp edges along an extended length.

As shown in FIG. 3A, one embodiment of a wire 32 can have a series of sharp edged protrusions 64 along an extended length of the distal end of the wire 32. This length of extension along which the protrusions 64 are provided may extend more than 1 cm or more than 5 cm from the tip of the wire 32. At the tip of the wire 32, a larger sharp edged protrusion 66 can be provided. If desired, although not illustrated in FIG. 3A, a larger sharp edged protrusion can advantageously be provided at one or more bends or corners 68 provided in the distal end of the wire 32. These sharp edges can cut and scrape the endothelium effectively, removing additional tissue. The spaces between the protrusions can retain endothelium tissue during the procedure.

Figures 3B, 3C:
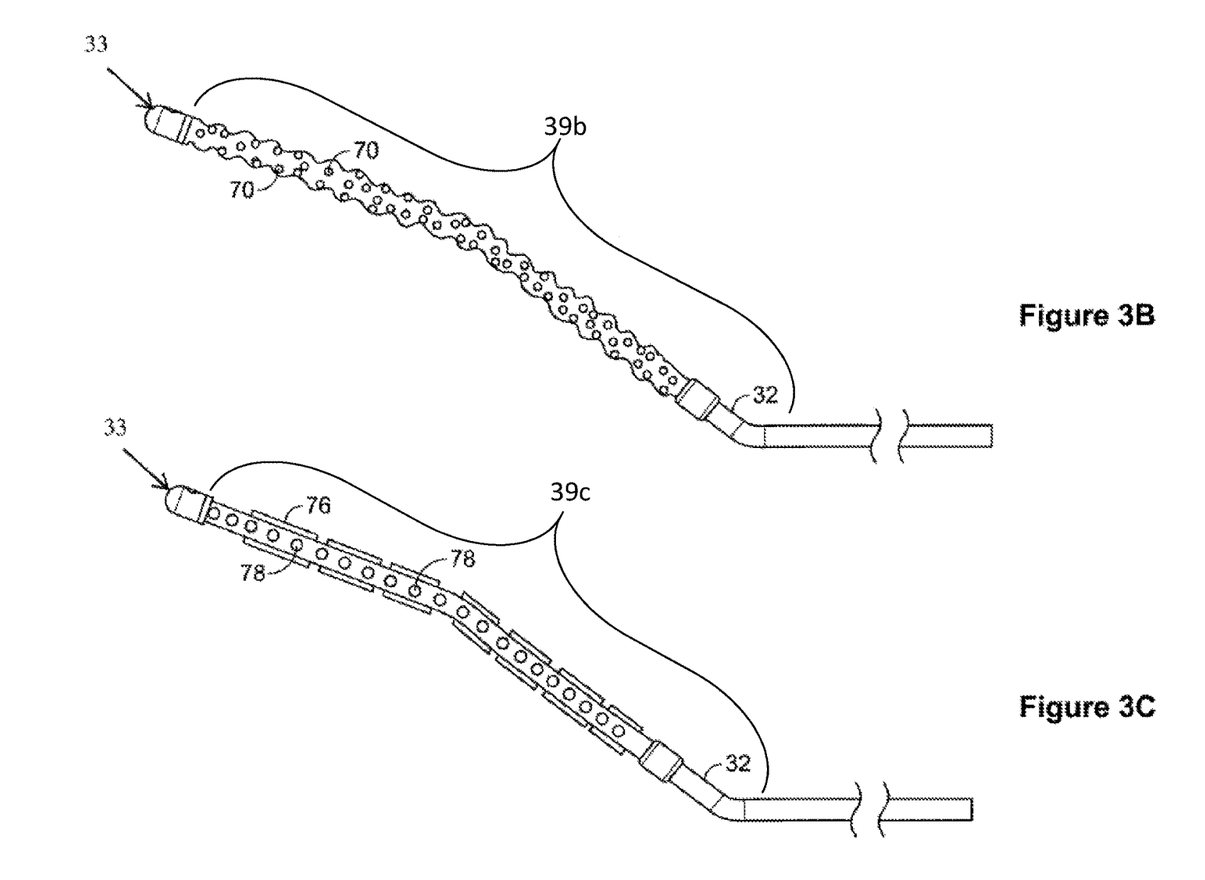
FIG. 3B illustrates an embodiment of a distal wire end having a roughened surface and cavities formed therein.
FIG. 3C illustrates an embodiment of a distal wire tip having scraping projections and cavities formed as through holes.

In the embodiment of FIG. 3B, an extended length of the distal end of the wire 32 (e.g. more than 1 cm or more than 5 cm) is provided with a roughened surface. A roughened surface may be formed by subjecting an initially smooth steel to abrasion, machining, blasting, chemical etching such as acid etching (for example, nitric acid, hydrofluoric acid, hydrochloric acid, and/or sulfuric acid). A roughened outer surface may also be created by rolling onto an irregularly shaped guide to create surface irregularity. The wire 32 of FIG. 3B also comprises relatively large cavities 70 that can retain endothelium tissue scraped off the inner vessel wall by the roughened surface.

In the embodiment of FIG. 3B, an extended length of the distal end 39b of the wire 32 (e.g. more than 1 cm or more than 5 cm) is provided with a roughened surface. A roughened surface may be formed by subjecting an initially smooth steel to abrasion, machining, blasting, chemical etching such as acid etching (for example, nitric acid, hydrofluoric acid, hydrochloric acid, and/or sulfuric acid). A roughened outer surface may also be created by rolling onto an irregularly shaped guide to create surface irregularity. The wire 32 of FIG. 3B also comprises relatively large cavities 70 that can retain endothelium tissue scraped off the inner vessel wall by the roughened surface.

In the embodiment of FIG. 3C, an extended length of the distal end 39c of the wire 32 (e.g. more than 1 cm or more than 5 cm) is provided with sharp edged protrusions 76, which may be formed as vanes or flanges extending from the sides of the wire 32. In this embodiment, cavities are provided as through holes 78 that can also retain endothelium tissue removed by the protrusions 76. It will be appreciated that any of the protrusions, cavities, roughened surface, etc. can be combined in a variety of manners on a single wire so that the distal end 39a-39c of the wire 32 is configured to both scrape away and retain endothelium tissue from the inner vessel wall during the procedure. Advantageously, catching and retaining of the endothelium can, in some embodiments, improve clinical results because scraping of tissue against tissue can cause significant abrasion to the vessel wall by increasing friction.

As shown in FIGS. 3B and 3C, the distal tip 33 of the wire 32 can be hemispherical. Alternatively, a pointed tip can be used. A hemispherical tip can also be roughened or textured. The distal end 39a-39c of the wire 32 can also incorporate curved segments and straight segments. A straight segment can be distal to a curved segment.

Figure 4:
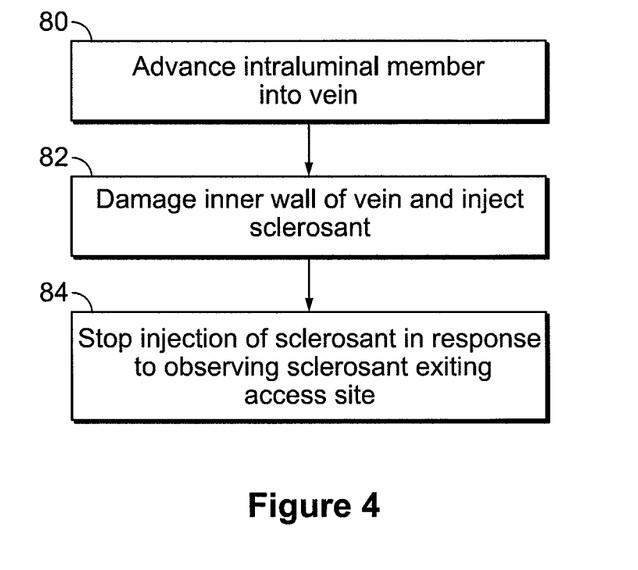
FIG. 4 is flow chart of a first vascular treatment method.

An ablation method can further include steps to protect against over-injection of sclerosant, into the deep system. In some embodiments, an operator can observe the insertion point of the ablation device, and upon observing exiting sclerosant, an operator can stop injection of additional sclerosant. This is illustrated by the procedure of FIG. 4. In this method, at block 80, the physician first advances the intraluminal member into the vein of the subject. At block 82, the physician damages the vein and injects sclerosant to ablate the vein as described above. At block 84, the physician stops injection of sclerosant in response to observing sclerosant exiting the vein through the intrlauminal member access point. Injection can be stopped manually, for example, stopping pushing on the plunger of the syringe 36 of FIG. 1 when sclerosant is observed exiting the access point. Advantageously, this protects against over-injection of sclerosant into the deep system, thus reducing complications of deep vein thrombosis.

Figure 5:
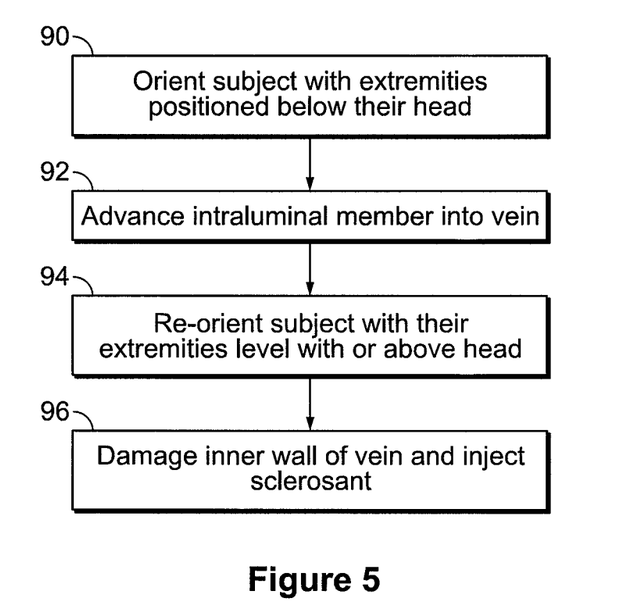
FIG. 5 is a flow chart of a second vascular treatment method.

In addition, methods of performing vessel ablation can include creating and maintaining specific patient positioning. A patient can be, for example, tilted to enable access to veins and then moved to a flat position for performing the vessel ablation. This is illustrated by the method shown in FIG. 5. In this method, at block 90, the subject is oriented with the extremity to be treated positioned below their head. This allows easy vein access for introducing the intraluminal member into the vein at block 92. After the intraluminal member is inserted, at block 94 the subject is re-oriented with the extremity being treated level with or above their head. The procedure is then continued at block 96 where the inner vein wall is damaged and sclerosant is injected as described above. Advantageously, a flat or slightly inclined patient position allows blood and injectant to spill toward the untreated vein as the treated area of the vein gradually occludes. In one embodiment for treatment of leg veins, the patient can be tilted with legs down to facilitate vein access. The patient is then moved into a flat or only slightly head-down position. Advantageously, use of such patient positioning increases success rates for the procedure by allowing blood and sclerosant to spill toward the untreated vein which increases vein ablation and decreases the risk of deep vein thrombosis. In prior vein ablation procedures, the extremity being treated was maintained in a position below the head. The combination of vessel damage with the injection of sclerosant, however, allows the lifting of the extremity during the procedure with improved outcomes.

The foregoing description details certain embodiments of the devices and methods disclosed herein. It will be appreciated, however, that no matter how detailed the foregoing appears in text, the devices and methods can be practiced in many ways. As is also stated above, it should be noted that the use of particular terminology when describing certain features or aspects of the invention should not be taken to imply that the terminology is being re-defined herein to be restricted to including any specific characteristics of the features or aspects of the technology with which that terminology is associated.

It will be appreciated by those skilled in the art that various modifications and changes may be made without departing from the scope of the described technology. Such modifications and changes are intended to fall within the scope of the embodiments. It will also be appreciated by those of skill in the art that parts included in one embodiment are interchangeable with other embodiments; one or more parts from a depicted embodiment can be included with other depicted embodiments in any combination. For example, any of the various components described herein and/or depicted in the Figures may be combined, interchanged or excluded from other embodiments.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

All references cited herein are incorporated herein by reference in their entirety. To the extent publications and patents or patent applications incorporated by reference contradict the disclosure contained in the specification, the specification is intended to supersede and/or take precedence over any such contradictory material.

The term "comprising" as used herein is synonymous with "including," "containing," or "characterized by," and is inclusive or open-ended and does not exclude additional, unrecited elements or method steps.

What is claimed is:

1. A vascular treatment apparatus comprising:
an elongated intraluminal member being shaped and dimensioned for passage through a blood vessel of a subject, the elongated intraluminal member being housed in a sheath when configured in a non-engaged position, the elongated intraluminal member extending between a proximal end and a distal end; and
a vein wall disruptor disposed on the distal end of the elongated intraluminal member, the vein wall disruptor comprising a wire comprising a first vane extending from a surface of the wire and a plurality of cavities disposed within the surface of the wire, the plurality of cavities extending along the surface for at least 1 cm from a distal tip of the wire, the vein wall disruptor extending from an interior portion of the sheath at an angle when configured in an engaged position, the vein wall disruptor being axially offset from the proximal end of the elongated intraluminal member when in the engaged position;
wherein the vein wall disruptor further comprises a second vane extending from the surface of the wire, wherein the first vane extends in a first direction and the second vane extends in a second direction that is opposite the first direction, and wherein each of the first vane and the second vane comprises a scraping surface configured to damage an inner wall of the blood vessel.

2. The apparatus according to claim 1, wherein the distal tip is hemispheric in shape.

3. The apparatus according to claim 2, wherein the distal tip further comprises an abrasive surface.

4. The apparatus according to claim 1, wherein the distal tip is pointed in shape.

5. The apparatus according to claim 1, wherein the plurality of cavities are configured to retain tissue from the inner wall of the blood vessel when the vein wall disruptor is operably engaged to damage the inner wall of the blood vessel.

6. The apparatus according to claim 1, wherein the distal end of the elongated intraluminal member comprises a curved segment.

7. The apparatus according to claim 6, wherein the distal end of the elongated intraluminal member comprises a straight segment distal to the curved segment.

8. The apparatus according to claim 1, additionally comprising: a source of sclerosant; and a fluid channel between the source of sclerosant and the distal end of the elongated intraluminal member.

9. The apparatus according to claim 8, wherein the fluid channel comprises a space between the sheath and the elongated intraluminal member.

10. The apparatus according to claim 9, wherein the apparatus is configured to inject sclerosant as the elongated intraluminal member rotates within the sheath.

11. The apparatus according to claim 1, wherein the plurality of cavities are through holes that extend through the wire.

12. The apparatus according to claim 1, wherein each of the first and second vanes comprises a sharp edged protrusion.

13. The apparatus according to claim 1, wherein the sheath comprises an inner diameter of 0.022 inches to 0.048 inches.

14. The apparatus according to claim 13, wherein the sheath comprises an outer diameter of 0.025 inches to 0.051 inches.

15. The apparatus according to claim 1, further comprising a motorized drive system.

16. The apparatus according to claim 15, further comprising a trigger and a handle, wherein pressing the trigger activates a motor of the motorized drive system.

17. The apparatus according to claim 15, wherein the motorized drive system comprises a battery.

18. The apparatus according to claim 1, wherein the elongated intraluminal member is rotatable within the sheath.

19. The apparatus according to claim 1, wherein the sheath comprises external markings for monitoring insertion or removal of the elongated intraluminal member.

20. The apparatus according to claim 1, wherein the plurality of cavities extend along the surface for at least 5 cm from the distal tip of the wire.

* * * * *